(12) United States Patent
Matsiev et al.

(10) Patent No.: US 7,254,990 B2
(45) Date of Patent: Aug. 14, 2007

(54) MACHINE FLUID SENSOR

(75) Inventors: Leonid Matsiev, San Jose, CA (US); James Bennett, Santa Clara, CA (US); Daniel M. Pinkas, Menlo Park, CA (US); Mikhail Spitkovsky, Sunnyvale, CA (US); Oleg Kolosov, San Jose, CA (US); Shenheng Guan, Palo Alto, CA (US); Mark Uhrich, Redwood City, CA (US); G. Cameron Dales, Saratoga, CA (US); John F. Varni, Los Gatos, CA (US); Blake Walker, Eugene, OR (US); Vladimir Gammer, San Francisco, CA (US); Dave Padowitz, Mountain View, CA (US); Eric Low, Berkeley, CA (US)

(73) Assignee: Visyx Technologies, Inc., Sunnyvale, CA (US)

( * ) Notice: Subject to any disclaimer, the term of this patent is extended or adjusted under 35 U.S.C. 154(b) by 0 days.

(21) Appl. No.: 11/433,265

(22) Filed: May 12, 2006

(65) Prior Publication Data

US 2006/0218996 A1   Oct. 5, 2006

Related U.S. Application Data

(62) Division of application No. 10/452,264, filed on Jun. 2, 2003, now Pat. No. 7,043,969.

(60) Provisional application No. 60/419,404, filed on Oct. 18, 2002.

(51) Int. Cl.
  *G01N 11/16* (2006.01)
(52) U.S. Cl. .................. 73/54.41; 73/53.05; 73/64.42
(58) Field of Classification Search ............... 73/24.06, 73/31.05, 30.04, 32 A, 54.24, 53.3, 54.41, 73/61.49, 61.75; 422/68.1
See application file for complete search history.

(56) References Cited

U.S. PATENT DOCUMENTS 3,273,377 A   9/1966 Testerman et al.

(Continued)

FOREIGN PATENT DOCUMENTS

DE   4424422   1/1996

(Continued)

OTHER PUBLICATIONS

Brand et al. "Micromachined Viscosity Sensor for Real-time Polymerization Monitoring," Jun. 16-19, 1997, "1997 International Conference on Solid-State Sensors and Actuators" pp. 121-124.*

(Continued)

*Primary Examiner*—Hezron Williams
*Assistant Examiner*—John Fitzgerald

(57) ABSTRACT

A sensor for sensing one or more properties of a vehicle fluid has a tuning fork resonator adapted to contact the fluid. The tuning fork resonator comprises two tines and is operable to oscillate so that the two tines move in opposite phase at a frequency of less than 1 MHz while contacting the fluid to generate a resonator response indicative of one or more properties of the fluid. In another aspect, a sensor includes a substrate and a flexural resonator on the substrate and adapted to contact the fluid. Circuitry for operation of the resonator is on the substrate. The resonator is adapted to receive an input signal and to oscillate while contacting the fluid to generate a resonator response indicative of one or more properties of the fluid. One suitable application for the invention is monitoring the condition of a vehicle engine oil.

43 Claims, 7 Drawing Sheets

U.S. PATENT DOCUMENTS

| | | | |
|---|---|---|---|
| 3,329,004 A * | 7/1967 | King, Jr. ................... 73/24.06 |
| 3,490,056 A * | 1/1970 | Milton et al. ............... 333/186 |
| 3,622,968 A | 11/1971 | Silverman |
| 3,710,275 A | 1/1973 | Tanaka et al. |
| 3,718,032 A | 2/1973 | Gray |
| 3,745,384 A * | 7/1973 | Blanchard .................. 310/324 |
| 3,762,197 A | 10/1973 | Roof et al. |
| 3,778,757 A | 12/1973 | Houston |
| 3,902,365 A | 9/1975 | Knauth |
| 3,903,732 A | 9/1975 | Rork et al. |
| 3,921,622 A | 11/1975 | Cole |
| 3,926,271 A | 12/1975 | Patashnick |
| 4,103,224 A | 7/1978 | Taro et al. |
| 4,145,922 A | 3/1979 | Estrada, Jr. et al. |
| 4,312,228 A * | 1/1982 | Wohltjen ..................... 73/597 |
| 4,342,936 A | 8/1982 | Marcus et al. |
| 4,349,881 A | 9/1982 | November et al. |
| 4,361,026 A | 11/1982 | Muller et al. |
| 4,370,662 A | 1/1983 | Hou et al. |
| 4,391,338 A | 7/1983 | Patashnick et al. |
| 4,498,025 A * | 2/1985 | Takahashi ................... 310/312 |
| 4,526,480 A * | 7/1985 | Ward ......................... 374/117 |
| 4,535,620 A | 8/1985 | Cunningham |
| 4,543,829 A | 10/1985 | Lerch |
| 4,549,427 A | 10/1985 | Kolesar, Jr. |
| 4,596,697 A | 6/1986 | Ballato |
| 4,602,505 A | 7/1986 | Kanda et al. |
| 4,624,129 A | 11/1986 | Haynes |
| 4,644,803 A | 2/1987 | Ward |
| 4,696,181 A | 9/1987 | Rupprecht et al. |
| 4,721,874 A | 1/1988 | Emmert |
| 4,729,237 A * | 3/1988 | Suzuki et al. ............... 73/54.02 |
| 4,734,609 A * | 3/1988 | Jasmine ..................... 310/315 |
| 4,741,200 A | 5/1988 | Hammerle |
| 4,760,351 A | 7/1988 | Newell et al. |
| 4,767,719 A | 8/1988 | Finlan |
| 4,779,451 A | 10/1988 | Ezawa et al. |
| 4,782,332 A | 11/1988 | Cipris et al. |
| 4,783,987 A | 11/1988 | Hager et al. |
| 4,802,370 A | 2/1989 | EerNisse et al. |
| 4,802,384 A | 2/1989 | Schwarz et al. |
| 4,812,698 A | 3/1989 | Chida et al. |
| 4,862,384 A | 8/1989 | Bujard |
| 4,890,480 A | 1/1990 | Young |
| 4,893,496 A | 1/1990 | Bau et al. |
| 4,904,978 A | 2/1990 | Barth et al. |
| 4,905,701 A * | 3/1990 | Cornelius ................... 600/437 |
| 4,910,523 A | 3/1990 | Huguenin et al. |
| 4,922,745 A | 5/1990 | Rudkin et al. ............... 73/32 A |
| 4,970,492 A | 11/1990 | King |
| 5,006,845 A | 4/1991 | Calcar et al. |
| 5,157,962 A * | 10/1992 | Fitzgerald et al. ......... 73/54.24 |
| 5,179,028 A * | 1/1993 | Vali et al. ................... 436/524 |
| 5,191,791 A | 3/1993 | Gerardi et al. |
| 5,201,215 A | 4/1993 | Granstaff et al. |
| 5,204,529 A | 4/1993 | Diatschenko |
| 5,212,987 A * | 5/1993 | Dransfeld et al. ............ 73/579 |
| 5,224,174 A | 6/1993 | Schneider et al. |
| 5,235,844 A | 8/1993 | Bonne et al. |
| 5,253,530 A | 10/1993 | Letcher, III |
| 5,279,162 A * | 1/1994 | Takebe et al. ................ 73/726 |
| 5,283,037 A | 2/1994 | Baer et al. |
| 5,296,374 A | 3/1994 | Culshaw et al. |
| 5,306,644 A | 4/1994 | Myerholtz et al. |
| 5,325,704 A | 7/1994 | Mariami et al. |
| 5,332,961 A | 7/1994 | Hammerle |
| 5,334,900 A | 8/1994 | Kawashima |
| 5,338,416 A | 8/1994 | Mlcak et al. |
| 5,357,964 A | 10/1994 | Spivey et al. |
| 5,361,632 A | 11/1994 | Magnani |
| 5,375,470 A | 12/1994 | Matsushima et al. |
| 5,421,190 A | 6/1995 | Brandle et al. |
| 5,434,650 A | 7/1995 | Nakahara et al. |
| 5,435,170 A | 7/1995 | Voelker et al. |
| 5,445,008 A | 8/1995 | Wachter et al. |
| 5,454,045 A | 9/1995 | Perkins et al. |
| 5,455,475 A | 10/1995 | Josse et al. |
| 5,464,509 A | 11/1995 | Mlcak et al. |
| 5,469,369 A | 11/1995 | Rose-Pehrsson et al. |
| 5,477,726 A | 12/1995 | Stabinger et al. |
| 5,488,866 A | 2/1996 | Ravel et al. |
| 5,524,477 A | 6/1996 | Wajid |
| 5,524,636 A | 6/1996 | Sarvazyan et al. |
| 5,528,924 A | 6/1996 | Wajid et al. |
| 5,531,091 A | 7/1996 | Gademann et al. |
| 5,533,402 A | 7/1996 | Sarvazyan et al. |
| 5,571,401 A | 11/1996 | Lewis et al. |
| 5,571,952 A * | 11/1996 | Kauzlarich ................. 73/54.24 |
| 5,604,441 A | 2/1997 | Freese, V et al. |
| 5,622,223 A | 4/1997 | Vasquez |
| 5,653,939 A | 8/1997 | Hollis et al. |
| 5,661,233 A | 8/1997 | Spates et al. |
| 5,670,709 A | 9/1997 | Gallagher |
| 5,698,089 A | 12/1997 | Lewis et al. |
| 5,705,399 A | 1/1998 | Larue |
| 5,734,098 A * | 3/1998 | Kraus et al. ............... 73/61.62 |
| 5,741,961 A | 4/1998 | Martin et al. |
| 5,741,962 A | 4/1998 | Birchak et al. |
| 5,744,902 A | 4/1998 | Vig |
| 5,770,038 A | 6/1998 | Iwama et al. |
| 5,776,359 A | 7/1998 | Schultz et al. |
| 5,777,210 A | 7/1998 | Voelker et al. |
| 5,789,665 A | 8/1998 | Voelker et al. |
| 5,792,938 A | 8/1998 | Gokhfeld |
| 5,798,452 A | 8/1998 | Martin et al. |
| 5,818,731 A | 10/1998 | Mittal et al. |
| 5,827,952 A | 10/1998 | Mansure et al. |
| 5,852,229 A * | 12/1998 | Josse et al. ................. 73/24.06 |
| 5,885,849 A | 3/1999 | Di Stephano et al. |
| 5,889,351 A | 3/1999 | Okumura et al. |
| 5,915,499 A | 6/1999 | Few |
| 5,918,354 A | 7/1999 | Ikegami et al. |
| 5,959,297 A | 9/1999 | Weinberg et al. |
| 5,985,356 A | 11/1999 | Schultz et al. |
| 6,023,961 A | 2/2000 | Discenzo et al. |
| 6,034,775 A | 3/2000 | McFarland et al. |
| 6,041,642 A | 3/2000 | Duncan |
| 6,044,694 A * | 4/2000 | Anderson et al. .......... 73/54.41 |
| 6,126,311 A | 10/2000 | Schuh |
| 6,151,123 A | 11/2000 | Nielsen |
| 6,155,098 A | 12/2000 | Shapiro et al. |
| 6,157,449 A | 12/2000 | Hajduk |
| 6,175,409 B1 | 1/2001 | Nielsen et al. |
| 6,176,323 B1 | 1/2001 | Weirich et al. |
| 6,182,499 B1 * | 2/2001 | McFarland et al. ......... 73/24.06 |
| 6,186,005 B1 * | 2/2001 | Leidl ........................... 73/597 |
| 6,223,589 B1 | 5/2001 | Dickert et al. |
| 6,247,354 B1 | 6/2001 | Vig et al. |
| 6,260,407 B1 | 7/2001 | Petro et al. |
| 6,260,408 B1 * | 7/2001 | Vig et al. ................... 73/64.53 |
| 6,265,226 B1 | 7/2001 | Petro et al. |
| 6,269,686 B1 * | 8/2001 | Hahn et al. ................. 73/54.24 |
| 6,275,137 B1 | 8/2001 | Doppalapudi et al. |
| 6,286,363 B1 | 9/2001 | Discenzo |
| 6,294,388 B1 | 9/2001 | Petro et al. |
| 6,296,771 B1 | 10/2001 | Miroslav |
| 6,306,358 B1 | 10/2001 | Yamamoto |
| 6,311,549 B1 | 11/2001 | Thundat et al. |
| 6,327,890 B1 | 12/2001 | Galipeau et al. |
| 6,336,353 B2 * | 1/2002 | Matsiev et al. ............. 73/24.06 |
| 6,371,640 B1 | 4/2002 | Hajduk |
| 6,386,053 B1 * | 5/2002 | Takeuchi et al. ............... 73/865 |
| 6,393,895 B1 * | 5/2002 | Matsiev et al. ............. 73/24.06 |
| 6,401,519 B1 * | 6/2002 | McFarland et al. ......... 73/24.06 |

| | | | |
|---|---|---|---|
| 6,407,479 B1 | 6/2002 | Moellendorf et al. | |
| 6,412,131 B1 | 7/2002 | Zhao et al. | |
| 6,424,074 B2* | 7/2002 | Nguyen | 310/309 |
| 6,441,716 B1 | 8/2002 | Doppalapudi et al. | |
| 6,456,096 B1 | 9/2002 | Ericson et al. | |
| 6,459,995 B1 | 10/2002 | Collister | |
| 6,494,079 B1* | 12/2002 | Matsiev et al. | 73/24.05 |
| 6,509,749 B1 | 1/2003 | Buelna et al. | |
| 6,511,915 B2 | 1/2003 | Mlcak | |
| 6,513,365 B1* | 2/2003 | Bruetting et al. | 73/32 A |
| 6,519,034 B1 | 2/2003 | Engler et al. | |
| 6,535,001 B1 | 3/2003 | Wang | |
| 6,536,634 B2 | 3/2003 | Berndorfer et al. | |
| 6,545,392 B2 | 4/2003 | Kawauchi et al. | |
| 6,557,396 B2 | 5/2003 | Ismail et al. | |
| 6,564,126 B1 | 5/2003 | Lin et al. | |
| 6,626,025 B2* | 9/2003 | Potyrailo et al. | 73/7 |
| 6,640,644 B1 | 11/2003 | Mireles et al. | |
| 6,644,095 B2 | 11/2003 | Van Mullekom et al. | |
| 6,661,162 B1 | 12/2003 | Nagai et al. | |
| 6,675,652 B2* | 1/2004 | Yamazaki | 73/504.16 |
| 6,734,762 B2* | 5/2004 | Cornett et al. | 333/186 |
| 6,931,927 B2* | 8/2005 | Ohta et al. | 73/504.16 |
| 6,938,470 B2* | 9/2005 | DiFoggio et al. | 73/152.24 |
| 7,043,969 B2* | 5/2006 | Matsiev et al. | 73/54.41 |
| 2001/0010174 A1 | 8/2001 | Matsiev et al. | |
| 2002/0064649 A1 | 5/2002 | Lembke et al. | |
| 2002/0068488 A1 | 6/2002 | Tuller et al. | |
| 2002/0070841 A1 | 6/2002 | Doppalapudi et al. | |
| 2002/0074897 A1 | 6/2002 | Ma et al. | |
| 2002/0092340 A1 | 7/2002 | Prater et al. | |
| 2002/0113596 A1 | 8/2002 | Horie et al. | |
| 2002/0121132 A1 | 9/2002 | Breed et al. | |
| 2002/0137348 A1 | 9/2002 | Mlack | |
| 2002/0148529 A1 | 10/2002 | Berndorfer et al. | |
| 2002/0162385 A1 | 11/2002 | Ismail et al. | |
| 2002/0162390 A1 | 11/2002 | Ismail et al. | |
| 2002/0178787 A1 | 12/2002 | Matsiev et al. | |
| 2002/0178805 A1 | 12/2002 | DiFoggio et al. | |
| 2002/0194906 A1 | 12/2002 | Goodwin et al. | |
| 2003/0000291 A1 | 1/2003 | Kolosov et al. | |
| 2003/0041653 A1 | 3/2003 | Matsiev et al. | |
| 2003/0041659 A1 | 3/2003 | Marszalek et al. | |
| 2003/0062910 A1 | 4/2003 | Wang et al. | |
| 2003/0083825 A1 | 5/2003 | Berndorfer | |
| 2003/0116497 A1 | 6/2003 | Carlson et al. | |
| 2003/0118078 A1 | 6/2003 | Carlson et al. | |
| 2003/0119060 A1 | 6/2003 | Desrosiers et al. | |
| 2003/0124028 A1 | 7/2003 | Carlson et al. | |
| 2003/0145647 A1 | 8/2003 | Ismail et al. | |
| 2003/0179002 A1 | 9/2003 | Beylich et al. | |
| 2003/0213292 A1 | 11/2003 | Budeiri et al. | |
| 2004/0255648 A1* | 12/2004 | Sparks | 73/54.41 |
| 2006/0230833 A1* | 10/2006 | Liu et al. | 73/649 |

FOREIGN PATENT DOCUMENTS

| | | |
|---|---|---|
| DE | 10014724 | 9/2001 |
| EP | 0102490 | 3/1984 |
| EP | 0282251 | 9/1988 |
| EP | 0317356 B1 | 5/1989 |
| EP | 0676638 | 10/1995 |
| EP | 0769695 A | 4/1997 |
| EP | 0779510 | 6/1997 |
| EP | 0813236 | 12/1997 |
| GB | 1385488 | 8/1971 |
| GB | 2114745 | 8/1983 |
| GB | 2187286 | 9/1987 |
| JP | 59126931 | 7/1984 |
| JP | 60134617 | 7/1985 |
| JP | 5129874 | 5/1993 |
| JP | 8112613 | 5/1996 |
| JP | 11094726 | 9/1997 |
| WO | WO 95/13278 | 5/1995 |
| WO | WO 98/01739 | 6/1997 |
| WO | WO 9801739 A2 * | 1/1998 |
| WO | WO 98/15501 | 4/1998 |
| WO | WO 98/37412 | 8/1998 |
| WO | WO 99/18431 | 4/1999 |
| WO | WO 00/58709 | 3/2000 |
| WO | WO 00/67086 | 11/2000 |
| WO | WO 01/77624 | 10/2001 |
| WO | WO 02/12265 | 2/2002 |
| WO | WO 02/16888 | 2/2002 |
| WO | WO 02/23134 | 3/2002 |
| WO | WO 02/077613 | 10/2002 |
| WO | WO 03/014732 | 2/2003 |
| WO | WO 03/054482 | 7/2003 |
| WO | WO 03/100390 A2 | 12/2003 |
| WO | WO 2004/036207 A2 | 4/2004 |

OTHER PUBLICATIONS

Zhang et al. "Determination of liquid density with low frequency mechanical sensor based on quartz tuning fork," Aug. 2001, Sensors and Actuators B 84, pp. 123-128.*

A&D Weighing, SV Series Users' Handbook V1.04E, p. 1-40, date unknown.

Akporiaye, D. et al. "Combinatorial Chemistry—The Emperor's New Clothes?", Microporous and Mesoporous Materials 48 (2001) 367-373.

"Automotive Engineering International Online: Top 50 Products for 1999", Product Info. List/Oil Quality Sensor, 1999, www.sae.org/automag/top50prod/17.htm, printed Feb. 5, 2004, p. 17.

Baltes H., Göpel W., Hesse J., Acoustic Wave Sensors, 1996, pp. 37-83, vol. 2, Chapter 2, ISBN: 3-527-29432-5, Sensors Update, VCH, Weinheim.

Barnes, C., "An in vitro urea sensor using a torsion-wave crystal device", Sensors and Actuators B, 8 (1992) 143-149.

Benes et al., "Sensors based on piezoelectric resonators", Sensors and Actuators A, May 1, 1995, pp. 1-21, vol. 48, No. 1, Elsevier Sequoia S.A., Lausanne.

Benes et al., "Viscosity Sensor Based on a Symmetric Dual Quartz Thickness Shear Resonator", pp. 1-7, 2003.

Bohmer, Elemente der angewandten Elektrotechnik, 1992, with English Translation.

Brand, Oliver, et al., "Micromachined Viscosity Sensor For Real-Time Polymerization Monitoring", Transducers '97 IEEE International Conference on Solid-State Sensors and Actuators, 1997, p. 121-124.

Chen, G.Y., et al., "Resonance response of scanning force microscopy cantilevers", Review of Scientific Instruments, Aug. 1994, p. 2532-2537, 65(8).

"CJV-5000 Vibro Viscometer Utilizing Tuning-Fork Technology", A&D Medical Weighing Test & Measurement Digital Testing and Measurement Products, Jan. 28, 2000.

Cleland, A.N. et al., "Fabrication of high frequency nanometer scale mechanical resonators from bulk Si crystals", Applied Physics Letters, Oct. 28, 1996, p. 2653-2655, 69(18).

"diScentris Cantilever Sensor Research Tool for Science and Industry", Veeco Instruments Inc. Brochure, 2003.

Dring et al., "Integrated on-line multisensing of fluid flow using a mechanical resonator", Sensors and Actuators A, Elsevier Sequoia S.A., Lausanne, CH, vol. 85, No. 1-3, Aug. 25, 2000, pp. 275-279.

Endo, H., et al., "Online Monitoring of the Viscosity in Dextran Fermentation Using Piezoelectric Quartz Crystal", Biotechnology and Bioengineering, vol. 36, S636-641 (1990).

"EPSON presents the MC-30A: Reliable 32.768kHz Dedicated to Automotive Applications", Aug. 25, 2003, Electronic Devices Press Release, www.epson.com.sq.ntml.body_ed_press_25_aug_2003.html, printed Feb. 11, 2004.

Ferry, John D., "Viscoelastic Properties of Polymers", Chapters 5-8, p. 96-176.

"Field Trials of the Viscosity & Fluid Density Tool", Nan Gall Technology News Releases, Aug. 2002, www.nangall.com/products/plt/Fluid_Density_Tuned.htm, printed Feb. 14, 2003.

Fisch, M.R. wt al., "Improved acoustic viscosimeter technique", Journal of the Acoustical. Society of America, Sep. 1976, p. 623-625, vol. 60, No. 3.

Fleming, "The Vibrating Tuning Fork Fluid Density Tool", p. H1-H15, Nan Gall Technology Ltd, Aberdeen, Smith Institute, date unknown.

Fleming, "Theory of the vibrating tuning fork fluid density tool", Mar. 15, 2002, www.lancs.ac.uk.depts/physics/conf/esgi/NanGall/transducer.htm, printed May 7, 2003.

Godemann, Ralph, "Refrigerant Flow in Evaporators", Heatcraft North America Transfer OEM Products Brochure, 2000, www.heatcraftoem.com/TechTopics/refrigerant_flow.htm.

Grate, et al., "Acoustic TSMSAWFPWAPM Wave Microsensors", Analytical Chemistry, Sep. 1, 1993, pp. 940A-948A, vol. 65, No. 21, American Chemical Society, Columbus, US.

Grate, et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition", Analytical Chemsitry, 1993, p. 1868-1881, vol. 65, No. 14.

Greenwood, M.S., et al., "Measurement of viscosity and shear wave velocity of a liquid or slurry for on-line process control", Ultrasonics 29 (2002), pp. 623-630.

Greenwood, M.S., et al, "On-line Sensor for Density and Viscosity Measurements of a Liquid or Slurry for Process Control in the Food Industry", P.E. Sixth Conference on Food Engineering, 1999, AIChE Annual Meeting, Dallas, Texas, abstract.

Hagood, Nesbitt, et al., "Development of Micro-Hydraulic Transducer Technology", 10th International Conference on Adaptive Structures and Technologies, Oct. 11-13, 1999, Paris, France.

Hammond et al, "An Acoustic Automotive Engine Oil Quality Sensor", Transducers '97, 1997 International Conference on Solid-State Sensors and Actuators, Chicago, Jun. 16-19, No. 1997, p. 1343-1346.

Hauptmann, Peter, et al., "Ultrasonic sensors for process monitoring and chemical analysis: state-of-the-art and trends", Sensors and Actuators, 1998, p. 32-48, A67.

Hlavay, J. et al., "Applications of the Piezoelectric Crystal Detector in Analytical Chemistry", Analytical Chemistry, Nov. 1977, p. 1890-1898, vol. 49, No. 13.

Hoenk, Michael, et al., "Surface Acoustic Wave Hygrometer: Measuring Water Vapor in Earth's Atmosphere", http://mishkin.jpl.nasa.gov , accessed Mar. 16, 2002, 7 pages.

Horine B. H.; Malocha D. C., Equivalent Circuit Parameter Extraction of SAW Resonators, Dec. 4, 1990, pp. 477-482.

Ito H., Nakazawa M., An analysis of impedance-gas pressure characteristics of tuning fork-type quartz vacuum gauge-the effects of the drag force and the viscous friction of gas, Electronics, and Communications in Japan, Feb. 1991, pp. 10-18, Part 3, vol. 74, Nr. 2, XP009044733, Fundamental Electronic Science.

Jakoby, et al., "Viscosity Sensing Using a Love Wave Device", Sensors and Actuators, 1998, p. 275-281, A68.

Kanazawa, K. et al., "The Oscillation Frequency of a Quartz Resonator in Contact with a Liquid", Analytica Chimica Acta, 1985, p. 99-105, 175, Elsevier Science Publishers B.V., Amsterdam.

Karrai, Khaled, "Lecture Notes on Shear and Friction Force Detection with Quartz Tuning Forks", Presented at the Ecole Thematique du CNRS on near-field optics, Mar. 2000, La Londe les Maures, France.

"@Kavlico . . . Our Sensors Are the Solution!", Kavlico, A Solectron Company, Capability Product Brochure—Industrial Sensors and Tranducers, date unknown.

Kipling, A. et al, "Network Analysis Method Applied to Liquid-Phase Acoustic Wave Sensors", Anal. Chem, 1990, pp. 1514-1519, 62.

Laine, E., et al., "Device for the Investigation of the Humidity-Related Behaviours of Materials", 1986, Department of Physics, Universityof Turku, Finland.

Landua, L.D., et al., "Fluid Mechanics", "Viscous Fluids; Oscillatory Motion in a Viscous Fluid", 1959, p. 96-97, Pergamon Press. Ltd.

Langdon, "Vibratory Process Control Transducers", The Marconi Review, Third Quarter, 1980, pp. 156-175.

Lec, R.M., et al., "A Remote Acoustic Engine Oil Quality Sensor", IEEE Ultrasonics Symposium, 1997, p. 419-422.

Li, et al., "Electromechanical Behavior of PZT-Brass Unimorphs", Journal of the American Ceramic Society, vol. 82, No. 7, 1999, pp. 1733-1740.

Lin, Z., et al., "Operation of an Ultrasensitive 30-MHz Quartz Crystal Microbalance in Liquids", Analytical Chemical, 1993, p. 1546-1551, 65.

Manalis, S.R., et al., "Two-dimensional micromechanical bimorph arrays for detection of thermal radiation", Applied Physics Letters, Jun. 16, 1997, p. 3311-3313, 70(24).

Martin, Bret A., et al., "Viscosity and Density Sensing with Ultrasonic Plate Waves", Sensors and Actuators, Mar. 1990, p. 704-708.

Martin S. J., Granstaff V.E., Frye G. C., Characterization Of A Quartz Crystal Microbalance With Simultaneous Mass And Liquid Loading, Analytical Chemistry, Oct. 15, 1995, pp. 2272-2281, vol. 63, Nr. 20, American Chemical Society, Columbus, US.

Mason, W.P., et al., "Measurement of the Viscosity and Shear Elasticity of Liquids by Means of a Torsionally Vibrating Crystal", Transactions of A.S.M.E., 69(1947) 359-370.

Matsiev, L.F, "Application of Flexural Mechanical Resonators to Simultaneous Measurements of Liquid Density and Viscosity", IEEE Ultrasonics Symposium, 1999, p. 457-460.

Merhaut, Josef, "Theory of Electroacoustics", "Theory of Mechanical Systems with Distributed Elements", 1981, p. 100-101, McGraww-Hill International Book Company.

Michels, A. et al., "1MHz quartz length extension resonator as a probe for scanning near-field acoustic microscopy", Thin Solid Films, (1995), p. 172-175, 264.

Muramatsu, et al., "Computation of Equivalent Circuit Parameters of Quartz Crystals in Contact with Liquids and Study of Liquid Properties", Analytical Chemistry, 1988, p. 2142-2146, 60.

Muramatsu, et al., "A quartz crystal viscosity sensor for monitoring coagulation reaction and its application to a multichannel coagulation detector", Biosensors & Bioelectronics, 1991, p. 353-358, 6.

Muramatsu, et al., "Viscosity Monitoring with a Piezoelectric Quartz Crystal and its Application to Determination of Endotoxin by Gelatin of Limulus Amebocyte Lysate", Analytica Chimica Acta, 1988, p. 91-87, 215.

Newsam, J. et al. "High Throughput Experimentation for the Synthesis of New Crystalline Microporous Solids," Microporous and Mesoporous Materials 48 (2001), 355-365.

Nomura, T. et al., Electrolytis Determination of Nanomolar Concentrations of Silver in Solution with a Piezoelectric Quartz Crystal, Analytica Chimica Acta, vol. 131 (1981), pp. 97-102, Elsevier Scientific Publishing Company.

NSF Award Abstract #0239151, Feb. 6, 2003, pp. 1-2.

Nussbaum, "An Accurate Non-Radioactive Fluid Density Sensor", presentation to the Society of Petroleum Engineers, Bergen, Norway, Apr. 2, 2003.

Oden, P.I., et al., "Viscous drag measurements utilizing microfabricated cantilevers", Applied Physics Letters, Jun. 24, 1996, p. 3814-3816, 68(26).

PM Lubricants Australia, "The Lubri-Sensor Electronic Oil Quality Analyser", www.pmlubricants.com, accessed on Feb. 5, 2004.

Polla, et al., "Processing and Characterization of Piezoelectric Materials and Integration into Microelectromechanical Systems", Annual Review of Materials Science, 1998, p. 563-597.

Pujari, et al., "Reliable Ceramics for Advanced Heat Engines", American Ceramic Society Bulletin, Apr. 1995, p. 86-90, vol. 74, No. 4.

Puuman, "Hygroscopicity Measurement Apparatus", date unknown, http://web.archive.org/web/20010405220058/www.puuman.com/hma.htm.

Sader, "Frequency response of cantilever beams immersed in viscous fluids with applications to the atomic force microscopy", Journal of Applied Physics, Jul. 1, 1998, p. 64-76, vol. 84 No. 1.

Schmitt, N., et al., "A new method based on acoustic impedance measurements for quartz immunosensors", Sensors and Actuators B43 (1997) 217-233.

"Sensors", www.izm.fhg.de/vu/seiten/seiten_nu/english/sensoren_e.html, accessed on Oct. 3, 2002, Fraunhofer Verbund Mikroelektronik.

"Sensors and Actuators INTELLEK Oil condition Sensor", DELPHI Corporation Energy and Chassis Systems.

Shih et al., Simultaneous Liquid Viscosity and Density Determination with Piezoelectric Unimorph Cantilevers: Journal of Applied Physics, American Institute of Physics, New York, U.S., vol. 89, No. 2, Jan. 15, 2001, pp. 1497-1505.

"SINIMS Oil and Gas Workshop", ICMS, Endinburgh, Mar. 11, 2002.

Surface Acoustic Wave (SAW) Hygrometer (Micro Weather Station), last updated Feb. 14, 2001, http://technology.jpl.nasa.gov/gallery/gl_pages/saw.html.

Smith et al., "Water Sorption Isotherms and Enthalpies of Water Sorption by Lysozyme Using the Quartz Crystal Microbalance/heat Conduction Calorimeter", Biochimica et Biophysica Acta, Oct. 4, 2001, pp. 150-159.

Sorab, J., et al., "Engine Oil Viscosity Sensors Using Disks of PZT Ceramic as Electromechanical Vibrators", Society of Automotive Engineers SAE, No. 971702, 1997.

"SOS Smart Oil Sensor", Impact Technologies LLC Brochure, 2003.

"The Future of Pressure and Temperature Measurement—A Lifetime of Accuracy" Senstronics Storm Brochure, date unknown.

Thompson, M., et al., Surface-Launched Acoustic Wave Sensors: Chemical Sensing and Thin-Film Characterization, Apr. 23, 1997, 112 pages, John Wiley & Sons, New York.

Trolier, Susan, et al., "Preparation of Chemically Etched Piezoelectric Resonators for Density Meters and Viscometers", Mat. Res. Bull., vol. 22, pp. 1267-1274.

Ulbricht, Helmar, Eningen, Crimpen-eine ausgereifte AnschluBtechnik, XP-000902731.

Valimaki, H., et al., "Evaluation of Equivalent Circuit Model for Thickness-Shear Mode Resonators in Liquids", Eurosensors X. Leuven, Belgium 11.9.1996, S1377-1380.

"ViscoMaster HFO Viscosity Transmitter for Marine and Power Applications", Solartron Mobrey Brochure, Jan. 2002.

Wright, Dr. Robert, et al., "Sensor Technology Improves Jet Engine Reliability", printed Feb. 5, 2004, www.afrlhorizons.com/Briefs/June01/PR0003.html, p. 1-2.

Wullner, D., et al. "Multi-Function Microsensor for Oil Condition Monitoring Systems", AMAA Paper 030305b, 2003, p. 1-5.

Zeisel et al, "A Precise and Robust Quartz Sensor Based on Tuning Fork Technology for ($SF_6$)-gas density control", Sensors and Actuators (2000) p. 233-236, vol. 80.

Zhang, et al., "Contributions of Amplitude Measurement in QCM Sensors", IEEE Transactions on Ultrasonics, Ferroelectrics, and Frequency Control, Sep. 1996, p. 942-947, vol. 43, No. 5.

Zhang, et al., "Determination of Liquid density with a low frequency mechanical sensor based on quartz tuning fork" Sensors and Actuators B, Elsevier Sequoia S.A. Lausanne, CH. vol. 84, No. 2-3, May 15, 2002, pp. 123-128.

\* cited by examiner

MACHINE FLUID SENSOR

CROSS-REFERENCE TO RELATED APPLICATION

This application is a division of patent application Ser. No. 10/452,264, filed Jun. 2, 2003, (to be issued May 16, 2006 as U.S. Pat. No. 7,043,969), which claims the benefit of Provisional Application Ser. No. 60/419,404, filed Oct. 18, 2002; the entire disclosures of which are hereby incorporated herein by reference.

TECHNICAL FIELD

The present invention generally relates to the field of fluid sensors and more particularly to an automotive fluid sensor incorporating a mechanical resonator.

BACKGROUND OF THE INVENTION

The use of a quartz oscillator in a sensor has been described in U.S. Pat. Nos. 6,223,589. 5,741,961 also discloses a quartz resonator for use in an engine oil sensor. Yet another piezoelectric sensor for engine oil is disclosed in Hammond, et al., "An Acoustic Automotive Engine Oil Quality Sensor", Proceedings of the 1997 IEEE International Frequency Control Symposium, IEEE Catalog No. 97CH36016, pp. 72-80, May 28-30, 1997.

An improved system for measuring characteristics of fluids using mechanical resonators is disclosed in commonly-owned U.S. Pat. Nos. 6,401,519; 6,393,895; 6,336,353; and 6,182,499.

The use of acoustic sensors has been addressed in applications such as viscosity measurement in "Acoustic Wave Microsensors," J. W. Grate, et al, Anal. Chem. 65, 940A-948A (1993)); "*Viscosity and Density Sensing with Ultrasonic Plate Waves*", B. A. Martin, S. W. Wenzel, and R. M. White, Sensors and Actuators, A21-A23 (1990), 704-708; "*Preparation of chemically etched piezoelectric resonators for density meters and viscometers*". S. Trolier, Q. C. Xu, R. E. Newnham, Mat. Res. Bull. 22, 1267-74 (1987); "*On-line Sensor for Density and Viscosity Measurement of a Liquid or Slurry for Process Control in the Food Industry*", Margaret S. Greenwood, Ph.D. James R. Skorpik, Judith Ann Bamberger, P. E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and "*Micromachined viscosity sensor for real-time polymerization monitoring*", O. Brand, J. M. English, S. A. Bidstrup, M. G. Allen, Transducers '97, 121-124 (1997).

Notwithstanding the above, there remains a need in the art for alternative or improved sensors for analyzing fluids used in machines (such as those in automotive systems), particularly for measuring changes in fluid amounts, changes in fluid quality or combinations thereof.

SUMMARY OF THE INVENTION

The present invention meets the above need by providing an improved fluid sensor, premised upon the employment of one or more sensitive mechanical resonators, whose resonance performance can be monitored and correlated with fluid characteristics.

In one aspect of the invention, a fluid sensor for sensing one or more properties of a fluid in a vehicle comprises a tuning fork resonator adapted to contact the fluid when the sensor is mounted on the vehicle. The tuning fork resonator comprises two tines and is operable when mounted on the vehicle to receive an input signal and to oscillate so that the two tines move in opposite phase at a frequency of less than 1 MHz while in contact with the fluid to generate a resonator response indicative of the one or more properties of the fluid.

In another aspect of the invention, a fluid sensor for sensing one or more properties of a fluid in a vehicle comprises a substrate. A flexural resonator is on the substrate. The flexural resonator is for contacting the fluid when the substrate and sensor are mounted on the vehicle. Circuitry for operation of the resonator is on the substrate. The resonator is adapted to receive an input signal and to oscillate while in contact with the fluid to generate a resonator response indicative of one or more properties of the fluid. The sensor includes at least one connector for connecting the flexural resonator with an input signal source on board the vehicle.

In still another aspect of the invention, a fluid sensor for sensing one or more properties of a fluid in a vehicle comprises a substrate. A flexural resonator is on the substrate for contacting the fluid when the substrate and sensor are mounted on the vehicle. Circuitry for operation of the resonator is on the substrate. The resonator is adapted to receive an input signal and to oscillate while in contact with the fluid to generate a resonator response indicative of properties of the fluid, including at least the density of the fluid and the viscosity of the fluid independent of the density.

In yet another aspect of the invention, a fluid sensor for sensing one or more properties of a engine oil in a vehicle comprises a substrate. A flexural resonator is on the substrate for contacting the fluid when the substrate and sensor are mounted on the vehicle. Circuitry for operation of the resonator is on the substrate. The resonator is adapted to receive an input signal and to oscillate while in contact with the fluid to generate a resonator response indicative of one or more properties of the fluid. The flexural resonator is coated with a material resistant to corrosion from the engine oil or to the build-up of contaminants present in the engine oil.

DETAILED DESCRIPTION OF THE PREFERRED EMBODIMENTS

Figure 1:
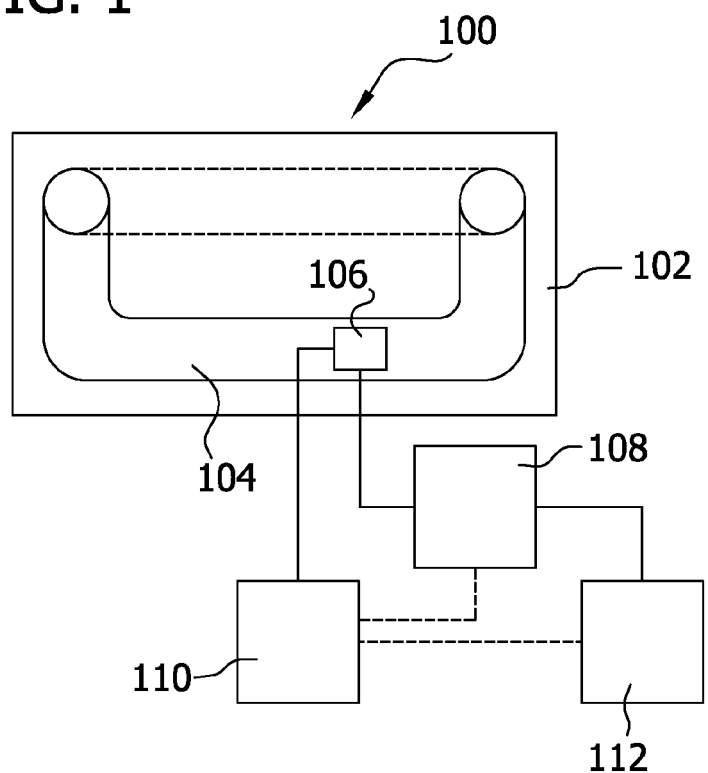
FIG. 1 shows a schematic view of one preferred system of the present invention.

As will be appreciated from the description herein, the present invention is directed primarily for analyzing one or more fluids that are contained (whether in a sealed system, an unsealed system or a combination thereof) in machines. One highly preferred use of the present invention is the analysis of one or more fluids (and particularly the viscosity, density or dielectric properties of one or more fluids) that are used in transportation vehicles (including, but not limited to, motorcycles, scooters, trucks, automobiles, construction equipment, locomotive, airplanes, boats, ships, farm machinery and/or spacecraft), such as fluids that are part of a sealed and/or self-contained operating system, and more preferably fluids that are part of a circulating or reservoir fluid system, such as engine oil, fuel, transmission oil, radiator fluid, power steering oil, hydraulic fluid, refrigerant, gear oil, brake fluid or the like. Accordingly, though illustrated herein in connection with such highly preferred use as in a transportation vehicle, the present invention has a wide variety of uses and the description is not intended to limit the invention herein disclosed.

The present invention is particularly attractive because of its ability to yield reproducible and reliable fluid analysis, particularly over a broad range of operation temperatures. It also affords a relatively low cost alternative to other existing sensors. In one particularly preferred embodiment, though not required in every embodiment, the sensors of the present invention can be operated with success at a relatively low frequency range.

One embodiment of the present invention is an improved method for analyzing a fluid contained within a machine. The method comprises the steps of providing a machine including a passage or reservoir for containing a fluid; placing a sensor including a mechanical resonator in the passage or reservoir; operating the resonator to have a portion thereof translate through the fluid; and monitoring the response of the resonator to the fluid in the passage or reservoir.

In another embodiment, the present invention is directed to a method for sensing a fluid in a circulating or reservoir fluid system, and includes the steps of providing a sealed circulating or reservoir fluid system; incorporating a mechanical resonator into the system, the mechanical resonator being in electrical communication with a source of an input signal; coupling the mechanical resonator with diagnostics hardware; exposing the fluid of the circulating or reservoir fluid system to the mechanical resonator; optionally applying an input signal; and monitoring a response of the mechanical resonator to the fluid with the diagnostics hardware.

When employed, the input signal for the sensors of the present invention may be any suitable signal. It may be generated from a direct current source or an alternating current source. It can be a constant frequency or a varying frequency. In one highly preferred embodiment, the signal is a varying frequency input signal. In another embodiment, the signal is a result of a voltage spike, sine wave burst, mechanical shock, pressure impulse, combinations thereof or the like.

The step of monitoring may be performed under any of a variety of different conditions. For example, in one embodiment, the monitoring step includes monitoring the change of frequency of the mechanical resonator while maintaining the input signal to the resonator as a constant. In another embodiment, the monitoring step includes monitoring the change in electrical feedback from the resonator while maintaining a constant frequency. In yet another instance, the monitoring can be in the substantial absence of a signal, where for example, the frequency change, the amplitude decay or both of a resonator is observed over a period of time after an input signal has been terminated.

The monitoring step will typically be guided by the nature of any input signal. In one highly preferred embodiment, for example, the monitoring step includes varying the frequency of a variable frequency input signal over a predetermined frequency range to obtain a frequency-dependent resonator response of the mechanical resonator.

The sensor of the present invention preferably includes at least one mechanical resonator, still more preferably one that is capable of operating at a frequency range less than 1 MHz. For example, a highly preferred resonator according to the present invention is operated at a frequency of less than 500 kHz, more preferably less than 100 kHz, and even still more preferably less than 75 kHz. A particularly preferred operational range is from about 1 kHz to about 50 kHz and more preferably about 5 to about 40 kHz. One highly preferred embodiment operates at about 20 to about 35 kHz.

Though other resonators are also possible, a preferred resonator is selected from the group consisting of tuning forks, cantilevers, bimorphs, and unimorphs. A highly preferred resonator is a tuning fork resonator.

The resonator may be uncoated or coated or otherwise surface treated over some or all of its exterior surface. A preferred coating is a metal, plastic, ceramic or composite thereof, in which the coating material is substantially resistant to degradation from the fluid to which it is to be exposed or to surface build-up, over a temperature range of about −10° to 100° C., and more preferably over a temperature range of about −40 to 125 or 150° C.

The structure of the resonator may be any suitable structure taking into account the specific environment into which it is to be introduced. As indicated, a preferred resonator is a tuning fork, and thus will include a plurality of tines projecting from a common base wherein the tines and base may be arranged in a variety of configurations.

It will be also appreciated that the resonator of the present invention, though potentially free standing, will generally be carried by a suitable support medium, such as a connector device for connecting the resonator with a source of an input signal, a device for monitoring the response of the resonator to the signal, or both. The nature of the connector device may vary from application to application. In one embodiment, it is a molded plastic (e.g., polyamide or the like) device into which electrical wires can be inserted in electrical communication with an inserted resonator. The connector may itself be configured for providing a suitable attachment (e.g., using a quick-connect mechanism) to a surface of the machine into which it is introduced. Alternatively, the connector may be adapted for insertion into, or otherwise may comprise, an integrated portion of a receptacle within the machine. It is also contemplated that the connector device, the receptacle or both may include a chip (e.g., a computer chip) for assisting in the communication of date to other components described herein.

The present invention is not limited to the use of a single resonator, but rather a plurality of resonators may be used. There may be plural resonators that are operational over the same or a different range of frequencies. There may be a plurality of resonators each of a different material or having a different coating or surface treatment. Plural resonators may be carried by a common carrier, or by separate carriers. Further, the resonators may be placed in the same general or proximate region of the machine or at remote locations relative to each other. An array of at least three resonators on a common carrier may also be employed.

One particularly preferred embodiment involves the incorporation of an oil sensor according to the present invention into an automotive vehicle engine. Thus, one possible approach is to locate the sensor in an engine oil pan. However, a sensor may be located in any other suitable oil passage in the engine.

The sensors of the present invention may be used continuously. Alternatively, a sensor can be disposable, so that at predetermined intervals it is removed and replaced with a different sensor.

The nature of the sensing that is performed by the sensor can be varied depending upon the parameter or condition that is desired to be monitored. Among the various applications are the use of the sensors herein for detecting the presence or absence of a fluid, the level of a fluid, the physical properties of a fluid, the presence of a contaminant in the fluid, the fluid pressure, the fluid flow rate, the fluid temperature, a change in physical property, condition or parameter of a fluid or a combination thereof.

Of course, basic conditions of the fluid such as viscosity, density, dielectric constant, conductivity or a combination thereof may also be monitored and reported, and in a highly preferred embodiment, these are the properties that are analyzed.

It is also possible that one of these latter basic conditions is monitored using one or more of the present sensors and the data output is processed by a suitable processing unit, which may apply an algorithm for correlating the outputted data with the presence or absence of a fluid, the level of a fluid, the replacement of a fluid, the presence of a contaminant in the fluid, the fluid pressure, the fluid flow rate, the fluid temperature, a change in the physical property, condition or parameter of a fluid or a combination thereof.

The step of monitoring may be performed under normal operating conditions of the machine into which the present sensor is placed. The present invention is particularly advantageous in that it is believed operable over a broad range of temperatures. Thus it is contemplated that the monitoring step occurs at a temperature below −40° C. or possibly the monitoring step occurs at a temperature above 125 or 150° C. Generally the monitoring will occur between these extremes.

It is also possible that during or following a monitoring step the response of the sensor is compared against a known reference value for the fluid. For example, in the context of an automotive engine oil, fresh oil can be analyzed upon its introduction into an engine. The observed response may then be stored in memory or otherwise recorded. Data about a particular fluid may be stored in memory of a suitable processor, which can be retrieved in response to a triggering event, such as input from a technician or reading of an engine oil type by an optical detector, such as a bar code scanner.

As the oil is used over a period of time, further analysis can be made and the response compared with that of the fresh oil. The identification of a difference between responses could then be used as a trigger or other output signal for communicating with diagnostics hardware, such as one or both of an on-board diagnostic device or operator interface (e.g., a dashboard display, an on board computer or the like), which would provide an audible or visual signal to the operator. It is also possible that a signal is outputted to a remote telemetry device, such as one located external of the vehicle. Thus, the signal that is outputted may be a radiofrequency signal or another wireless signal.

In one preferred embodiment, an output signal triggers an engine control unit to alter one or more functions (e.g., air intake, timing, or the like) of the engine or a combination thereof.

Comparisons of the response of the sensor to a reference value from the original fluid is not the only approach for generating a communication to a user about the fluid condition. Certain expected values may be pre-programmed into a device, which then compares the real-time values obtained to the expected values. Moreover, it is possible that no comparisons are made between real-time values and expected values, but rather upon obtaining a certain threshold response, an output signal is generated for triggering a user notification, for triggering an engine control unit to alter one or more functions of the engine or a combination thereof. It is also contemplated that a sensor in a controlled fluid sample may be employed as an internal reference.

It is also possible that the response obtained from the monitoring is stored in a memory, with or without communicating the response to the user. In this manner, a service technician can later retrieve the data for analysis.

Though illustrated in connection with an automotive vehicle, as with all such examples herein, it should be appreciated that such illustrations are not limited only to automotive vehicles, but that, as with the example just provided, like steps can be performed with other machines and motorized vehicles for transportation, hauling, lifting or performing mechanized work.

Referring to FIG. 1, there is illustrated one preferred system 100 of the present invention. The system 100 includes a component 102 having passages 104 therein through which a fluid is passed. Disposed within one of the passages 104 is at least one sensor 106, which is in signaling communication with a computer, controller or other like device 108. Preferably the sensor is also in signaling communication with a suitable power source 110. Diagnostics hardware 112 optionally may be incorporated into the device 108, or maintained separately from it. Suitable readout electronics may optionally be employed as part of or separate from the diagnostics hardware, e.g., including a readout board for interfacing between the computer and the resonator. Alternatively, a readout device may be associated with an instrument panel, such as for visual display to the operator of the machine or vehicle.

It will be appreciated that the above configuration permits the use of one or more measurement modes (which can be measured using electrical techniques, optical techniques or a combination thereof) such as excitation at one or more frequencies around resonance, passive oscillations due to ambient noise, vibrations, EMI or the time decay of oscillation after an electrical or mechanical impulse (e.g., a voltage spike).

It should be appreciated that, by use of the term "passage" herein, it is not intended to limit to structures that would be defined by walls of a conduit. Passage may include a reservoir, a well, an open-channel, a closed-channel, a container, or the like. Thus, generally the term "passage" herein contemplates any structure into which a fluid may be introduced, contained temporarily, contained permanently, passed through, removed from or otherwise.

Incorporation of a sensor into an automotive vehicle is in accordance with the inventive principles herein. It will be appreciated that the location of the resonator, or plurality of resonators, may be any suitable location for the intended measurement such as (among others) an engine oil pan, an oil sump, a pump, an oil filter device, an engine head, an engine block, a transfer case differential housing, a fluid line or hose, a heat exchanger, a dipstick, a drain plug, a sensor housing, or any other suitable location. Preferably the resonator is surface mounted, suspended or both, and positioned so that is analytical capability is not substantially compromised by fluid velocity, turbulence, mechanical oscillations, harmonics, vibrations or other extreme operating conditions. If it is necessary to subject a sensor to an extreme operating condition, then preferably the resonator will be suitably housed (e.g., in an enclosed chamber) or otherwise shielded as described herein.

Diagnostics hardware for use in monitoring the response of a resonator according to the present invention may comprise any suitable art-disclosed hardware, and the discussion herein is not intended as limiting. Without limitation, it is possible to employ hardware such as disclosed in commonly owned U.S. Pat. Nos. 6,401,519; 6,393,895; 6,336,353; and 6,182,499, hereby incorporated by reference. Another approach herein for measurement hardware is to employ an electrical readout system in communication with a computer and any resonators. For example, one or more hard-wired circuits may be employed, or more preferably, one or a plurality of printed circuit boards are employed to comprise the readout board, thereby affording a compact and reliable structure.

It should be appreciated that the discussion herein, in conformance with the drawings is specifically addressed to a system including one sensor adapted for analysis of a single fluid. However, the invention is not intended to be limited thereby, and it will be appreciated that the present invention also covers the use of a plurality of different sensors for measuring one fluid or a plurality of different fluids.

Figure 2:
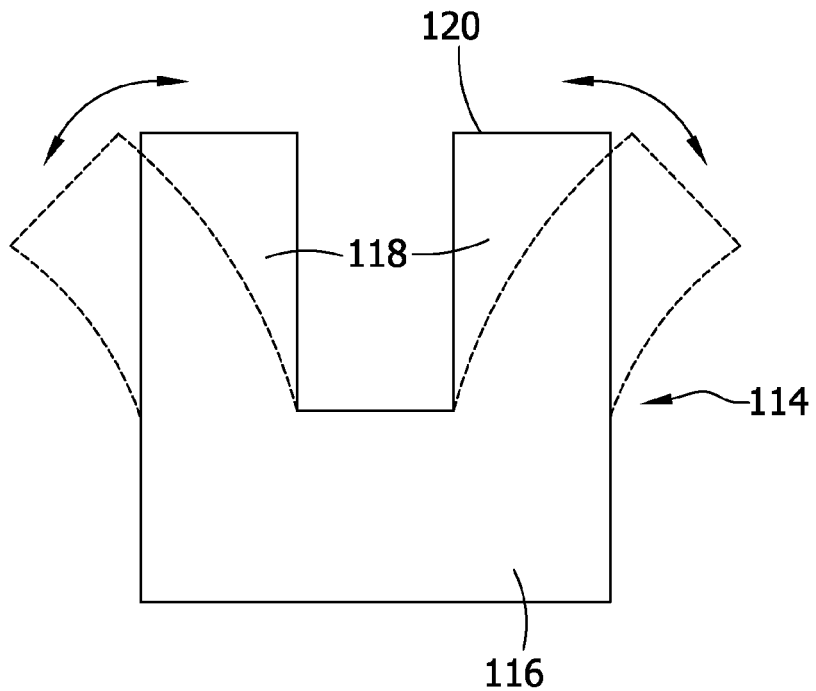
FIG. 2 shows a view of an illustrative resonator element of the present invention.

FIG. 2 illustrates one preferred resonator comprising a resonator element 114. The resonator element 114 preferably includes a base 116 that has at least two tines 118 having tips 120 that project from the base. The shape of the tines and their orientation relative to each other on the base may vary depending upon the particular needs of an application. For example, in one embodiment, the tines 118 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator elements are suitably positioned in an element holder that is built into the component 102. Alternatively, the elements (with or without a holder) may be securely attached to a wall or other surface defining one of the passages 104. In yet another embodiment, the element is suitably suspended within a passage 104, such as by a wire, screen, or other suitable structure.

Element holders may partially or fully surround the resonator elements as desired. Suitable protective shields, baffles, sheaths or the like may also be employed, as desired, for protection of the resonator elements from sudden changes in fluid flow rate, pressure or velocity, electrical or mechanical bombardment or the like. It should be appreciated that resonator elements may be fabricated from suitable materials or in a suitable manner such that they may be re-useable or disposable.

Figure 8:
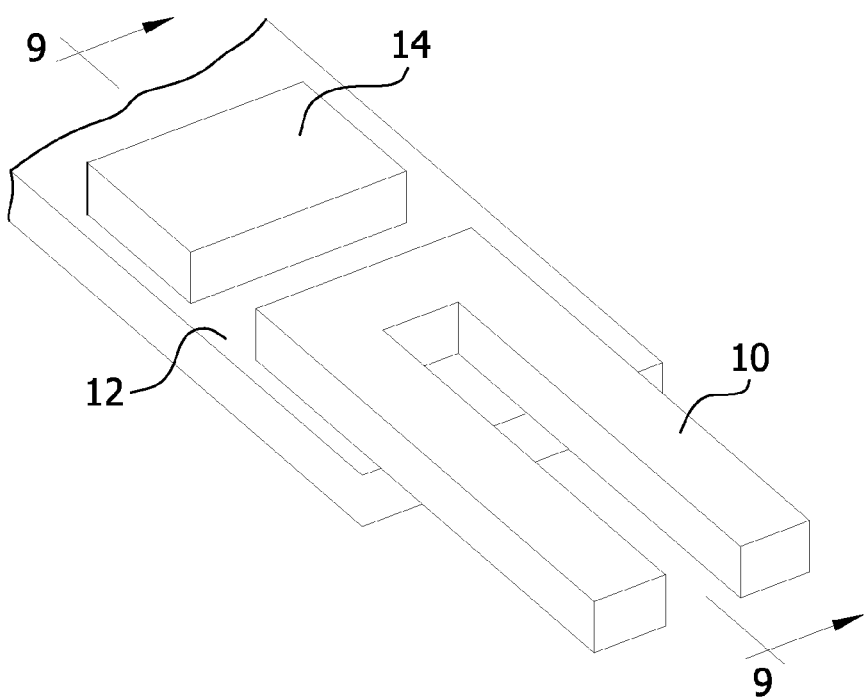
FIGS. 8 and 9 are schematic illustrations of a tuning fork resonator and circuitry mounted on a common substrate.
Figure 9:
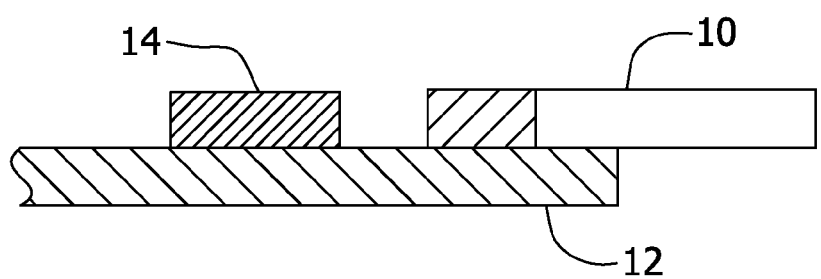

One or both of the resonator element holders preferably is configured with suitable hardware so that the resonator can be connected in signaling communication with an input signal source, an output analyzer or a combination thereof. One preferred construction (illustrated schematically in FIGS. 8 and 9) thus contemplates a device in which an exposed resonator 10 is formed integrally with or attached to a chip 12 or like surface mountable substrate that optionally has suitable circuitry 14 built thereon. The chip 12, in turn, may also include other sensing elements, or may be attached in signaling communication with another substrate having sensing elements associated with it.

For example, an existing device for sensing fluid temperature, fluid level or both, may be adapted so that the sensor of the present invention (such as one for sensing oil condition) is housed along with the other sensing elements. All of the elements may connect to a common carrier or substrate, or be enclosed in a common housing (e.g., an enclosure having one or more openings to allow a fluid to pass through the enclosure). Of course, the sensor can also be employed as a stand-alone sensor, and not need to be housed with other sensing elements.

The materials of the resonators of the present invention preferably are selected from at least one of piezoelectric materials, electrostrictive materials, magetostrictive materials, piezoresistive materials, elasto-optic materials, anisotropic materials, or combinations thereof. By way of example, the particular material may be a metallic material, a crystalline material, a ceramic material or a combination thereof. Examples of suitable materials include, without limitation, quartz, lithium niobate, zinc oxide, lead zirconate titanate (PZT) or the like.

Any suitable technique may be used to manufacture the resonator. For example, in one aspect, the resonators are prepared by art-disclosed processing techniques, such as are practiced in the semiconductor device fabrication industry. Thus, a wafer may be provided, one or more layers deposited thereon (e.g., by vapor deposition, sputtering, spin coating, curtain coating, laminating wafer bonding, or the like). Steps may be performed for shaping the resonator, such as photolithography, laser cutting, etching, dicing or the like. Other fabrication techniques, such as casting, molding, or the like may also be used.

A highly preferred embodiment of the present invention contemplates employing a tuning fork as a resonator. Preferably a two tine tuning fork is employed as the resonator. However, the method and system of the present invention can use any type of tuning fork resonator, such as a trident (three-prong) tuning fork or tuning forks of different sizes, without departing from the spirit and scope of the invention.

As indicated, the present invention is not intended to be limited to tuning fork resonators. Other types of resonators can be used, such as tridents, cantilevers, torsion bars, bimorphs, membrane resonators, torsion resonators, unimorphs or combinations thereof. Still other types of resonators can be used if modified from their conventional art disclosed forms or if they are used in combination with a preferred resonator. Examples of such resonators include thickness shear mode resonators, length extension resonators, various surface acoustic wave devices or combinations thereof. A plurality of the same type or different types of resonators can be used in combination. For example, a low frequency resonator may be employed with a high frequency resonator. In this manner, it may be possible to obtain a wider range of responses for a given sample.

Specifically it is preferred that the resonator of the sensors of the present invention are mechanical resonators, and more preferably flexural resonators, torsional resonators or a combination thereof. In one embodiment, preferred resonators may be selected from the group consisting of tuning forks, cantilevers, unimorphs, bimorphs, disc benders, and combinations thereof.

The size of the resonators can be varied. However, it should be appreciated that one advantage of the present invention is the ability to fabricate a very small sensor using the present resonators. For example, one preferred resonator has its largest dimension smaller than about 2 cm, and more preferably smaller than about 1 cm. One preferred resonator has length and width dimensions of about 2 mm by 5 mm, and possibly as small as about 1 mm by 2.5 mm.

Figure 3A:
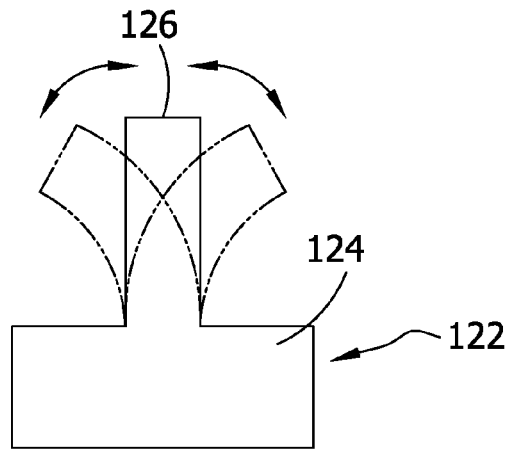
FIGS. 3A-3G illustrate alternative structures for a resonator according to the present invention.

It is thus seen that a preferred resonator is configured for movement of a body through a fluid. Thus, for example, as seen in FIG. 2, the resonator 114 may have a base 116 and one or a plurality of tines 118 projecting from the base. It is preferred in one aspect that any tine 118 has at least one free tip 120 that is capable of displacement in a fluid relative to the base 116. FIG. 3A illustrates a cantilever 122 having a base 124 and a free tip 126. Other possible structures, seen in FIGS. 3B and 3C contemplate having a disk 128, a plate 130 or the like that is adapted so that one portion of it is displaceable relative to one or more variable or fixed locations (e.g., 132 in FIG. 3B) (e.g., 132' in FIG. 3C). As seen in FIG. 3D, in yet another embodiment a resonator 134 is contemplated in which a shear surface 136 of the resonator has one or more projections 138 of a suitable configuration, in order that the resonator may be operated in shear mode while still functioning consistent with the flexural or torsional resonators of the present invention, by passing the projections through a fluid.

Figure 3B:
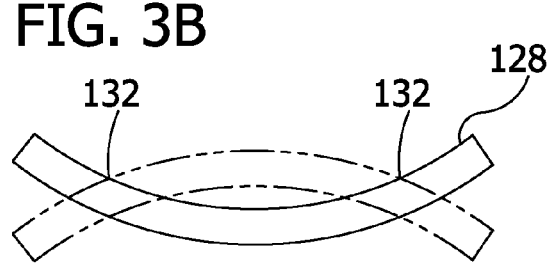
Figure 3C:
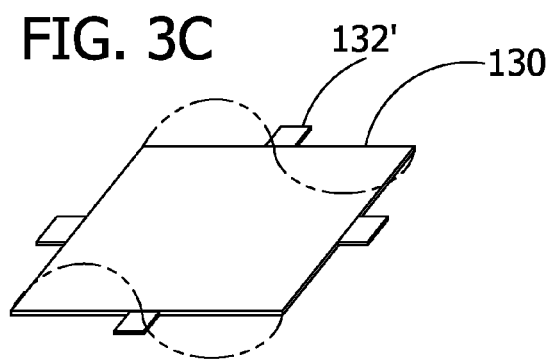
Figure 3D:
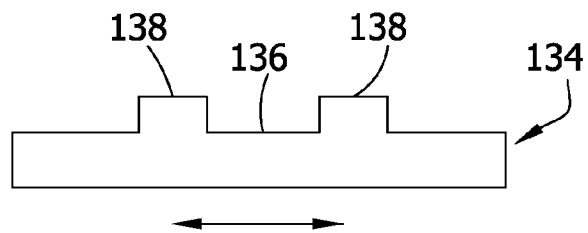
Figure 3E:
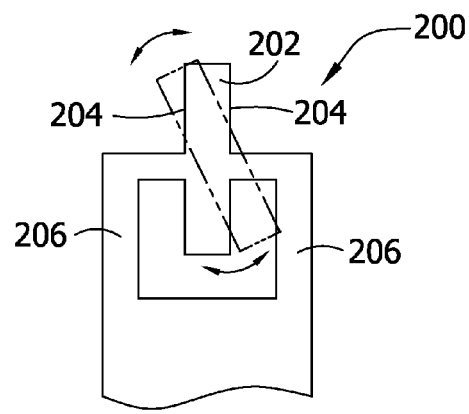
Figure 3F:
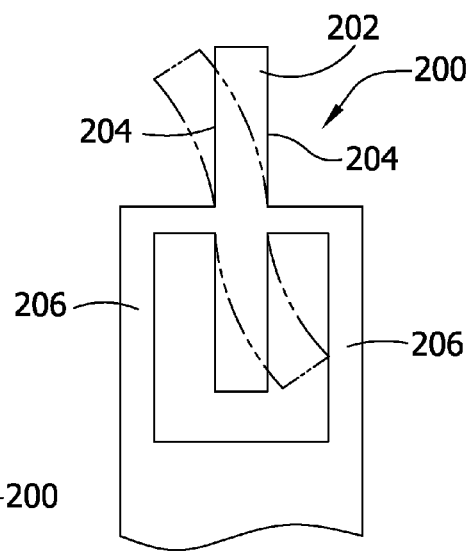
Figure 3G:
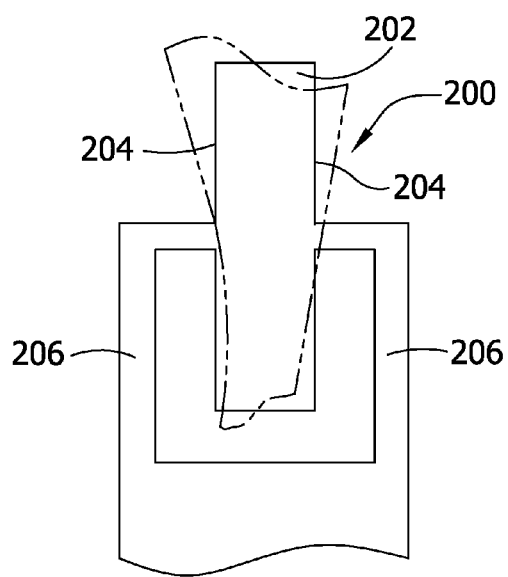

In still other embodiments, and referring to FIG. 3E-3G, it is contemplated that a resonator 200 may include an elongated member 202 supported on its sides 204 by a pair of arms 206. As shown respectively in FIGS. 3E-3G, the elongated member may be configured to oscillate side-to-side, back and forth, in twisting motions or combinations thereof.

The embodiment of FIG. 3B may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, one of the materials will respond differently than the other and the difference in responses will, in turn, result in the flexure of the resonator.

As can be seen, the selection of the specific resonator material, structure, or other characteristic will likely vary depending upon the specific intended application. Nonetheless, it is preferred that for each application, the resonator is such that one or a combination of the following features (and in one highly preferred embodiment, a combination of all features) is present:

1) a coating placed upon the resonator in thickness greater than about 0.1 micron that will not substantially detract from resonance performance;
2) the resonator is operable and is operated at a frequency of less than about 1 MHz, and more preferably less than about 100 kHz;
3) the resonator is substantially resistant to contaminants proximate to the sensor surface;
4) the resonator operates to displace at least a portion of its body through a fluid; or
5) the resonator responses are capable of de-convolution for measuring one or more individual properties of density, viscosity, or dielectric constant.

Also as discussed, in certain instances it is preferable for the resonator to be optionally coated with a material to change the performance characteristics of the resonator. For example, the material can be a coating, such as to protect the resonator from corrosion, degradation or other factors potentially affecting resonator performance. Alternatively, it may be a specialized "functionalization" coating that changes the resonator's response if a selected substance is present in the composition being tested by the resonator. For example, adding a hydrophobic or hydrophilic functionality to a resonator tine allows the tine to attract or repel selected substances in the fluid being analyzed, changing the mass, effective mass, geometry or a combination thereof of the tuning fork and thereby changing its resonance frequency.

Thus, in one particularly preferred embodiment the resonators used in the present invention include a surface that is substantially resistant to contaminant build-up (e.g., impurities, soot, varnish, sludge, or the like) over all or a portion thereof. Accordingly, it is preferred that at least a portion of the resonator surface includes a material or texture that exhibits a relatively low affinity to a contaminant, a relatively high affinity to the fluid under test, a relatively high degree of hydrophobicity, or a combination thereof. Under separate circumstances, however, it may be desirable that the resonator surface include a material or texture that exhibits a relatively high affinity to a contaminant, and a relatively high degree of hydrophillicity.

It is possible to achieve this by the selection of a resonator material that meets this requirement. Alternatively, a resonator may be suitably coated over at least a portion of its surface with a coating for exhibiting high hydrophobicity, a low coefficient of friction, or a combination thereof. Examples of suitable coating materials include, for example, fluoropolymers (e.g., PTFE), polyolefins (e.g., HDPE, HDPP or the like), silicones, silanes, siloxanes, ceramics (e.g., silicon nitride), diamond, or the like.

Coating thickness is not critical for most contemplated applications. However, a preferred coating thickness ranges from about 0.1 microns to about 10 microns. One embodiment contemplates a thickness of about 1 micron.

The resonators can also be functionalized with a polymer layer or other selective absorbing layer to detect the presence of specific molecules. The coating or functionality can be applied onto the resonator using any known method, such as physical vapor deposition (PVD), chemical vapor deposition (CVD), plasma enhanced chemical vapor deposition (PECVD), pulsed laser deposition (PLD), spraying or dipping. Further, the specific material selected for the coating or functionality will depend on the specific application in which the tuning fork resonator is to be used.

A single resonator may be coated or functionalized. Alternatively, multiple resonators having the same or a different structure but different coatings and/or functionalities can be incorporated into one sensor. For example, a plurality of resonators may have the same structure but have different functionalities, each functionality designed to, for example, bond with a different target molecule. When the sensor is used in such an application, one resonator can, for example, be functionalized with a material designed to bond with a first substance while another resonator can be functionalized with a material designed to bond with second substance. The presence of either one of these substances in the sample composition being tested will cause the corresponding resonator to change its resonance frequency. It is also possible to employ one or more sensors in which one resonator is coated, and another is not coated.

As discussed elsewhere, the manner of operating the sensors of the present invention may vary. In one embodiment, the sensor is operated continuously. In another, it may be intermittently operated. In other embodiments, the sensor may be operated only in preselected conditions, such as prior to starting vehicle operation, upon starting vehicle operation, during vehicle operation upon concluding vehicle operation, while the vehicle travels at a substantially constant velocity, while the vehicle accelerates or decelerates, or otherwise.

Under any or all of the above conditions, it will be recognized that the integrity of the measurement may be impaired as a result of some environmental condition, such as temperature. The present invention thus also contemplates as one of its embodiments, the employment of an environment conditioner, pursuant to which at least the environment proximate the location of the sensor is monitored or controlled to a predetermined condition. For example, it may be preferred with certain sensors to maintain the optimal sensing capability to be within a certain range of temperatures. A fluid that is outside of that range preferably will be detected and a temperature regulating device will heat or cool the fluid appropriately so that it can be efficiently sensed by the resonators of the present invention.

It is also possible that the environmental conditioner is operated to maintain the environment in a constant condition. In this manner, it can be seen, for example, that it is possible to employ a sensor of the present invention with a suitable heater for heating a frigid fluid to a certain temperature and preferably maintaining the fluid at that temperature for the duration of a measurement.

The use of an environmental conditioner also offers the advantage that certain properties of the sensed fluid that are sensitive to environmental conditions (e.g., viscosity, which is sensitive to temperature) will be relatively unaffected during measurements, and provide a more reproducible and reliable data.

Accordingly, in one preferred embodiment, the present invention contemplates operation of the sensor while the temperature of the sensed fluid is controlled at a substantially constant temperature by natural heat generated during normal vehicle operation, operation with local heating of the fluid or otherwise.

Figure 4A:
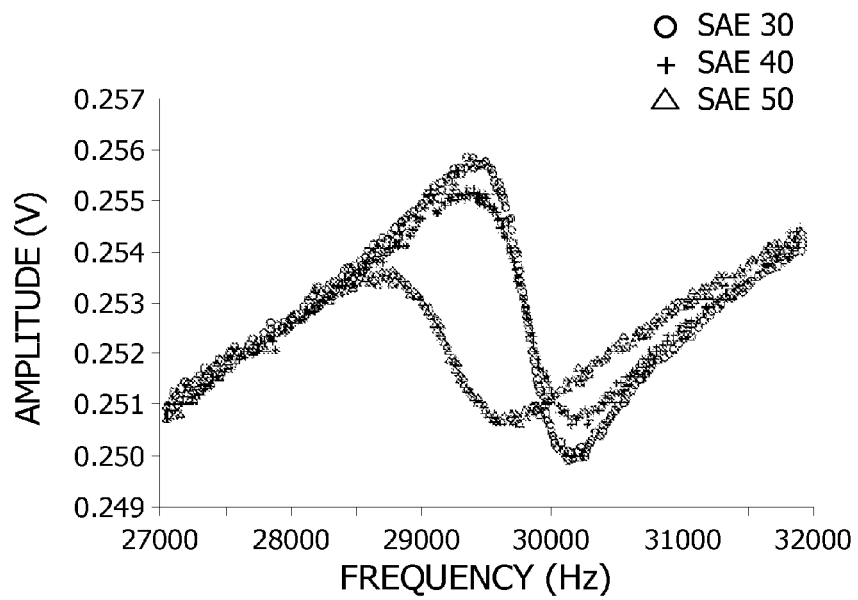
FIGS. 4A and 4B depicts an illustrative graphical display of data in accordance with the present invention.
Figure 4B:
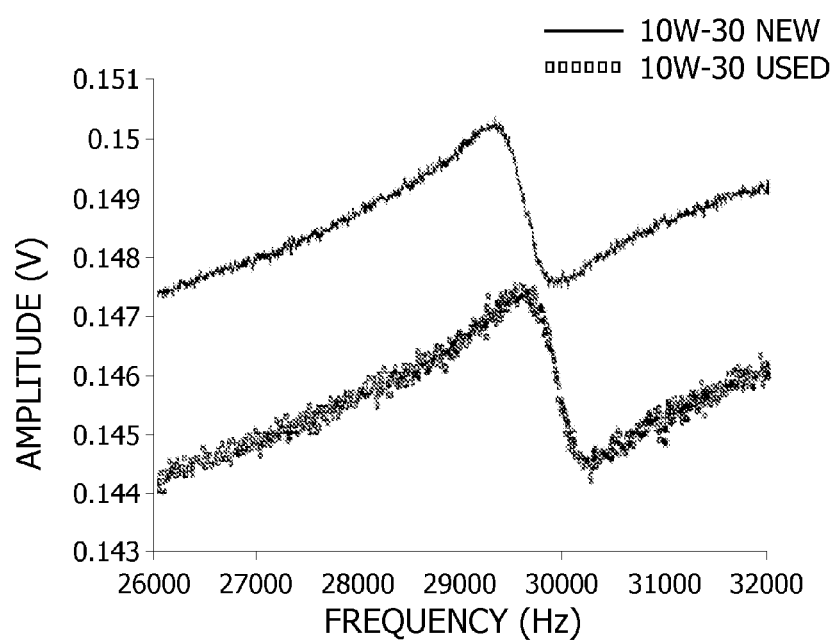

In certain instances, it is contemplated that data obtaining from the sensors may be graphically displayed, such as on a video display screen (e.g., a desk-top screen, a hand-held screen, or both). It may also be outputted in printed format. FIGS. 4A and 4B are exemplary displays of data obtained in accordance with the present invention. Though illustrating results comparing new and used engine oils, and different types of oils, like results are believed possible for other fluids, and at other frequencies.

Figure 5:
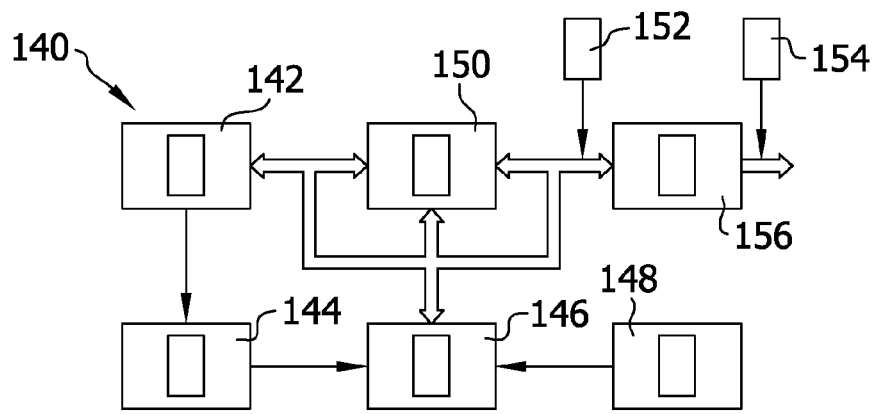
FIG. 5 is a schematic of one system employing a sensor according to the present invention.
Figure 6:
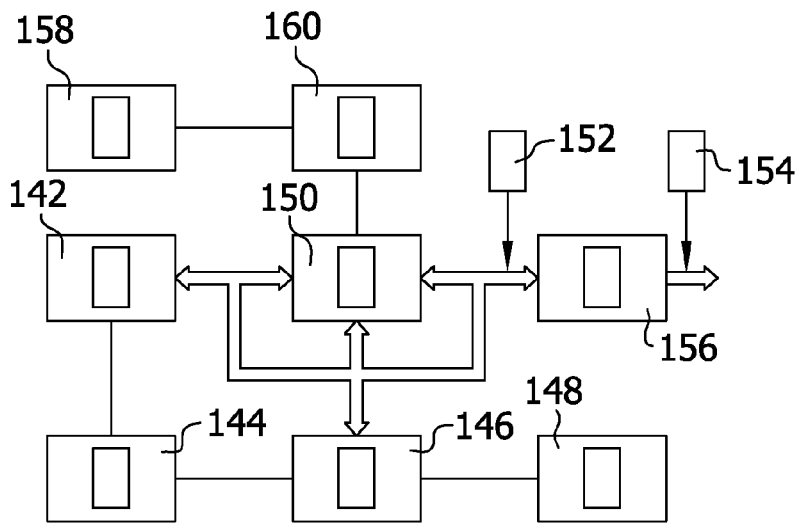
FIG. 6 is a schematic of an alternative system employing a sensor according to the present invention.

Examples of suitable systems that may be employed herein include the systems illustrated in FIGS. 5 and 6.

FIG. 5 illustrates a system 140 that employs a sweep oscillator 142 in signaling communication with a resonator 144. The signal generated from the resonator is transmitted to an analog-to-digital converter 146. Data from another sensor 148 (e.g., a temperature sensor) may also be sent to the converter 146. The converter 146, the sweep oscillator 142 or both communicate with a suitable processor 150 (e.g., an embedded microcontroller), which in turn is in signaling communication with one or both of an internal bus 152 or external bus 154, via for example a suitable interface 156 (e.g., a CAN interface).

FIG. 6 is substantially identical as FIG. 5 (with like parts denoted by like reference numerals), but further includes a suitable environmental conditioner 158 driven by a suitable driver 160 in communication with the processor 150.

It will be appreciated from the foregoing that, in one preferred embodiment, the present invention is employed for sensing viscosity of a machine fluid, and is founded upon analysis of changes in resonance characteristics that occur when the resonator is in contact with a fluid. The response is thus correlated with one or more fluid properties. Without intending to be bound by theory, to help with such a correlation, in a highly preferred embodiment, applicable to highly preferred resonators in accordance herewith, a mathematical or equivalent electrical circuit model can be constructed that includes the mechanical and electrical characteristics of the resonator, the properties of the surrounding fluid, and the coupling between resonator and fluid. Comparison of the model to measured data can help to yield the properties of interest. The parameters of the model can be found by fitting to the measured response using standard data fitting methods, such as (without limitation) least squares minimization. In one procedure, the parameters corresponding to the resonator alone are first determined by calibration in air or vacuum. A second calibration in a liquid of known properties such as viscosity, density, dielectric constant or a combination thereof, gives parameters for mechanical and electrical coupling between resonator and liquid. With the model parameters then established, the properties of other liquids can be determined. Data acquisition and analysis can be simplified for incorporation in a fluid monitoring system.

Figure 7:
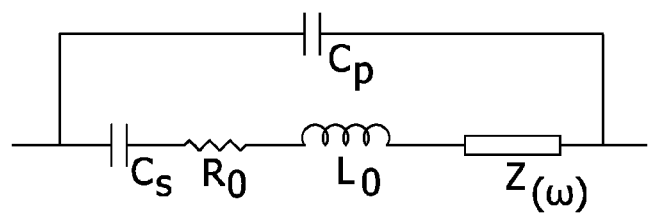
FIG. 7 illustrates an example of an equivalent circuit in accordance with the present invention.

An example of one such analysis is set forth in L. F. Matsiev, "*Application of Flexural Mechanical Resonators to Simultaneous Measurements of Liquid Density and Viscosity*", IEEE Ultrasonics Symposium Proceedings, pp. 457-460 (1999), hereby incorporated by reference. By way of illustration, for the equivalent circuit depicted in FIG. 7, it is assumed that $C_s$, $R_0$, $L_0$ are equivalent characteristics of a preferred resonator in a vacuum, $C_p$ is the equivalent parallel capacitance, $\rho$ is the liquid density, $\eta$ is liquid viscosity, $\omega$ is oscillation frequency.

Accordingly, it can be seen that viscosity and density can be de-convoluted by the following:

$$Z(\omega) = Ai\omega\rho + B\sqrt{\omega\rho\eta}(1+i)$$

$$Z(\omega) = i\omega\Delta L + \Delta Z\sqrt{\omega}(1+i)$$

$$\Delta L = A\rho, \Delta Z = B\sqrt{\rho\eta}$$

The above is not intended as limiting of the present invention. Other alternative models might be derived with reference to publications such as "Frequency response of cantilever beams immersed in viscous fluids with applications to the atomic force microscope", J. E. Sader, J. Appl. Phys. 84, 64-76 (1998); "Resonance response of scanning force microscopy cantilever", G. Y. Chen, R. J. Warmack, T. Thundat, and D. P. Allison, Rev. Sci. Instrum. 65, 2532-2537 (1994); and "Lecture notes on shear and friction force detection with quartz tuning forks" Work presented at the "Ecole Thématique du CNRS" on near-field optics, March 2000, La Londe les Maures, France by Khaled Karrai, Center for NanoScience, Section Physik der Ludwig-Maximilians-Universität München D-80539 München, Germany, the teachings of which are hereby incorporated by reference.

Further, it will also be appreciated that the above protocol need not be performed in every instance. For example, where the specifics of the resonator geometry and electronics are accurately known, a reduced set of measurements, such as the frequency and amplitude of the resonance peak and minimum could suffice to determine particular liquid properties. In this case, simplified detector electronics and analysis methods advantageously might be employed to facilitate incorporation in a system for on-line or real time fluid condition monitoring, which is also contemplated herein.

The sensors in accordance with the present invention advantageously provide excellent performance characteristics. Without limitation, for example, the sensors herein require less than 5V AC of excitation voltage, and on the order of less than 1 micro-amp current (e.g., about 0.1 micro-amps). Accurate measurements are obtainable in less than one second, and often less than about 0.25 seconds. The measurement range for viscosity is from about 0 to at least about 20 cPs (and possibly as high as at least about 5000 cPs) at 1 $g/cm^3$. The measurement range for density is from about 0 to at least about 20 $g/cm^3$ at 1 cP. Dielectric constants are measurable over at least the range of about 1 to about 100. Resolution (density,viscosity) values of less than 1% are also possible.

It will be further appreciated that functions or structures of a plurality of components or steps may be combined into a single component or step, or the functions or structures of one step or component may be split among plural steps or components. The present invention contemplates all of these combinations.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A fluid sensor for sensing one or more properties of a fluid in a vehicle, said sensor comprising:
    a tuning fork resonator for contacting said fluid when the sensor is mounted on the vehicle,
    said tuning fork resonator comprising two tines and being operable when mounted on said vehicle to receive an input signal and to oscillate so that the two tines move in opposite phase at a frequency of less than 1 MHz while in contact with said fluid to generate a resonator response indicative of said one or more properties of said fluid.

2. The fluid sensor of claim 1 further comprising a holder for holding said tuning fork resonator in a position for contact with said vehicle fluid, said holder being configured for attachment to said vehicle.

3. The fluid sensor of claim 1 wherein said tuning fork resonator is mounted on a surface mountable substrate, and wherein said sensor further comprises circuitry on said substrate.

4. The fluid sensor of claim 1 wherein said one or more fluid properties includes at least the density of the fluid and the viscosity of the independent of the density.

5. The fluid sensor of claim 1 wherein the tuning fork resonator comprises one or more layers deposited on a wafer shaped to form said tuning fork resonator.

6. The fluid sensor of claim 1 wherein the tuning fork resonator is mounted on said vehicle.

7. The fluid sensor of claim 1 wherein the tuning fork resonator comprises a base and tines of a piezoelectric or crystalline material.

8. The fluid sensor of claim 7 further comprising a plurality of electrodes, each of the tines having at least one electrode attached thereto.

9. The fluid sensor of claim 8 wherein the two tines each comprise four faces, each of the faces having an electrode attached thereto.

10. The fluid sensor of claim 1 wherein the tuning fork resonator is coated over at least a portion of its surface.

11. The fluid sensor of claim 10 wherein said vehicle fluid is engine oil, and wherein the tuning fork resonator is coated with a material resistant to corrosion from the engine oil or to the build-up of contaminants present in the engine oil.

12. The fluid sensor of claim 10 wherein the tuning fork resonator is coated with a hydrophobic material.

13. The fluid sensor of claim 1 further comprising at least one connector for connecting the tuning fork resonator with a source of said input signal on board said vehicle.

14. The fluid sensor of claim 13 wherein said at least one connector is configured for connecting said tuning fork resonator to a processor on board said vehicle for processing said response of the tuning fork resonator to measure said or more properties of said fluid.

15. The fluid sensor of claim 1 further comprising a housing for housing said tuning fork resonator, said housing being configured for attachment to said vehicle and having one or more openings for allowing said vehicle fluid to pass therethough.

16. The fluid sensor of claim 15 wherein said surface mountable substrate is a computer chip.

17. The fluid sensor of claim 1 wherein the resonator response is indicative of an electrical property of the fluid and at least one of a viscosity and a density of the fluid.

18. The fluid sensor of claim 17 wherein the electrical property is a dielectric constant of the fluid.

19. The fluid sensor of claim 17 wherein the resonator response is indicative of the viscosity and the density of the fluid.

20. A fluid sensor for sensing one or more properties of a fluid in a vehicle, said sensor comprising:
    a substrate;
    a flexural resonator on the substrate for contacting said fluid when the substrate and sensor are mounted on the vehicle; and
    circuitry on the substrate for operation of the resonator, said resonator being adapted to receive an input signal and to oscillate while in contact with said fluid to generate a resonator response indicative of said one or more properties of said fluid,
    wherein said vehicle fluid is engine oil, and wherein the flexural resonator is coated over at least a portion of its surface with a material resistant to corrosion from the engine oil or to the build-up of contaminants present in the engine oil.

21. The fluid sensor of claim 20 wherein the substrate is mounted on said vehicle.

22. The fluid sensor of claim 20 wherein said substrate is a computer chip.

23. The fluid sensor of claim 20 wherein the resonator response is indicative of an electrical property of the fluid.

24. The fluid sensor of claim 23 wherein the electrical property is a dielectric constant of the fluid.

25. The fluid sensor of claim 20 wherein the flexural resonator is a tuning fork resonator.

26. The fluid sensor of claim 25 wherein the tuning fork resonator comprises a base and tines of a piezoelectric or crystalline material.

27. A fluid sensor for sensing one or more properties of a fluid in a vehicle, said sensor comprising:
    a substrate;
    a flexural resonator on the substrate for contacting said fluid when the substrate and sensor are mounted on the vehicle;
    circuitry on the substrate for operation of the resonator, said resonator being adapted to receive an input signal and to oscillate while in contact with said fluid to generate a resonator response indicative of said one or more properties of said fluid; and at least one connector for connecting the flexural resonator with a source of said input signal on board said vehicle.

28. The fluid sensor of claim 27 wherein the substrate is a computer chip.

29. The fluid sensor of claim 27 wherein the flexural resonator is coated over at least a portion of its surface.

30. The fluid sensor of claim 27 wherein the substrate is mounted on said vehicle.

31. The fluid sensor of claim 27 wherein the flexural resonator is a tuning fork resonator.

32. The fluid sensor of claim 31 wherein the tuning fork resonator comprises a base and tines made of a piezoelectric or crystalline material.

33. The fluid sensor of claim 27 wherein the resonator response is indicative of an electrical property of the fluid and at least one of a viscosity and a density of the fluid.

34. The fluid sensor of claim 33 wherein the electrical property is a dielectric constant of the fluid.

35. The fluid sensor of claim 33 wherein the resonator response is indicative of the viscosity and the density of the fluid.

36. A fluid sensor for sensing one or more properties of a fluid in a vehicle, said sensor comprising:
   a substrate;
   a flexural resonator on the substrate for contacting said fluid when the substrate and sensor are mounted on the vehicle; and
   circuitry on the substrate for operation of the resonator, said resonator being adapted to receive an input signal and to oscillate while in contact with said fluid to generate a resonator response indicative of said one or more properties of said fluid,
   wherein said one or more fluid properties includes at least the density of the fluid and the viscosity of the fluid independent of the density.

37. The fluid sensor of claim 36 wherein the flexural resonator is coated over at least a portion of its surface.

38. The fluid sensor of claim 36 wherein the substrate is a computer chip.

39. The fluid sensor of claim 36 wherein the substrate is mounted on said vehicle.

40. The fluid sensor of claim 36 wherein the flexural resonator is a tuning fork resonator.

41. The fluid sensor of claim 40 wherein the tuning fork resonator comprises a base and tines made of a piezoelectric or crystalline material.

42. The fluid sensor of claim 36 wherein the resonator response is indicative of an electrical property of the fluid.

43. The fluid sensor of claim 42 wherein the electrical property is a dielectric constant of the fluid.

* * * * *